United States Patent [19]

Lippert et al.

[11] Patent Number: 5,917,085
[45] Date of Patent: Jun. 29, 1999

[54] CONTINUOUS PREPARATION OF METHYL FORMATE

[75] Inventors: Ferdinand Lippert, Bad Dürkheim; Arthur Höhn, Kirchheim; Jürgen Dahlhaus, Limburgerhof, all of Germany

[73] Assignee: BASF Aktiengesellschaft, Ludwigshafen, Germany

[21] Appl. No.: 08/875,657

[22] PCT Filed: Feb. 13, 1996

[86] PCT No.: PCT/EP96/00598

§ 371 Date: Jul. 30, 1997

§ 102(e) Date: Jul. 30, 1997

[87] PCT Pub. No.: WO96/26178

PCT Pub. Date: Aug. 29, 1996

[30] Foreign Application Priority Data

Feb. 24, 1995 [DE] Germany .......................... 195 06 555

[51] Int. Cl.$^6$ ..................................................... C07C 67/36
[52] U.S. Cl. ............................................................ 560/232
[58] Field of Search ................................................ 560/232

[56] References Cited

U.S. PATENT DOCUMENTS

| 4,661,624 | 4/1987 | Chang et al. | 560/232 |
| 5,401,873 | 3/1995 | Zehner et al. | 560/232 |

FOREIGN PATENT DOCUMENTS

| 596483 | 5/1994 | European Pat. Off. . |
| 1147214 | 4/1963 | Germany . |

*Primary Examiner*—Samuel Barts
*Assistant Examiner*—Rosalynd Keys
*Attorney, Agent, or Firm*—Keil & Weinkauf

[57] ABSTRACT

In a process for the continuous preparation of methyl formate by reaction of carbon monoxide and methanol under elevated pressure and elevated temperature in the presence of an alkali metal methoxide, the reaction is carried out at a pressure of from 210 to 250 bar in the presence of from 0.05 to 0.2% by weight of alkali metal methoxide, based on methanol used.

8 Claims, No Drawings

CONTINUOUS PREPARATION OF METHYL FORMATE

The present invention relates to an improved continuous process for preparing methyl formate by reaction of carbon monoxide and methanol under elevated pressure and elevated temperature in the presence of an alkali metal methoxide as catalyst.

The principle of this method of preparing methyl formate has long been known.

Methyl formate is processed into formic acid on an industrial scale. For this purpose, methyl formate is, prior to a hydrolysis step, separated by distillation from the catalyst and higher-boiling byproducts. The bottom product formed in the distillation cannot be recirculated to the reaction. In the case of sodium methoxide being used as catalyst, it contains sodium hydroxide, sodium formate, sodium carbonate and sodium oxalate, as well as other compounds. In continuously operated plants, these salts have to be disposed of, which incurs considerable costs because of the organic compounds present in the distillation bottoms (content of total organic carbon, TOC), which compounds have to be degraded in an effluent treatment plant.

DE-A 926 785 teaches a process for preparing methyl formate from methanol and carbon monoxide in the presence of at most 0.25% by weight of sodium, corresponding to 0.59% by weight of sodium methoxide, based on methanol used. The document discloses a reaction pressure of 300 bar. However, the space-time yields achievable under these conditions are unsatisfactory. A further disadvantage is that the reaction mixture obtained has to be pumped in a circuit outside the reactor to remove heat.

DE-A 11 47 214 teaches the splitting of the carbon monoxide stream in the preparation of methyl formate into two substreams which are fed to the reactor at different levels.

According to this document, from 0.12 to 0.3 mol% of catalyst are used, corresponding to over 0.2% by weight of sodium methoxide or 0.26% by weight of potassium methoxide, based on methanol used. The reaction pressure is from 150 to 200 bar. After prolonged operation, this procedure too results in encrustations of decomposition products of the catalyst on heat exchangers and reactor walls.

DE-A 43 09 731 relates to a process method according to which methanol and carbon monoxide are partially reacted in a mixing zone, the mixture thus obtained is saturated with carbon monoxide and the reaction is then completed in a post-reaction zone without a further supply of starting compounds. The reaction pressure is preferably a typical pressure for low-pressure processes of from 40 to 100 bar. The alkali metal methoxide concentration is preferably from 0.4 to 1.5% by weight, based on methanol used.

The reaction procedures described lead to the above-described formation of distillation bottoms which require cost-intensive disposal.

It is an object of the invention to keep the disposal costs for said distillation bottoms as low as possible. In particular, a way is to be found of reducing the formation of organic salts in these distillation bottoms.

We have found that this object is achieved by a continuous process for preparing methyl formate by reaction of methanol and carbon monoxide under elevated pressure and elevated temperature in the presence of alkali metal methoxide, wherein the reaction is carried out at a pressure of from 210 to 250 bar in the presence of from 0.05 to 0.2% by weight of alkali metal methoxide, based on methanol used.

The carbon monoxide used in the process of the invention can be mixed with inert gases such as nitrogen. However, the carbon monoxide content of the mixture of carbon monoxide and inert gases is preferably at least 93% by volume. To keep the hydrolytic decomposition of the catalyst low, the water content of the gas should be less than 100 ppm.

The catalyst used is an alkali metal methoxide such as sodium methoxide, preference being given to potassium methoxide. The catalyst is used in an amount of from 0.05 to 0.2% by weight, based on methanol used. The catalyst is advantageously introduced into the reaction zone in methanol solution.

Carbon monoxide, methanol and catalyst are mixed in the reaction zone, with good dispersion of the gas making a rapid reaction possible. For example, the gas can be introduced into the reactor through a nozzle. Methanol and the catalyst are preferably conveyed in countercurrent to the carbon monoxide. The carbon monoxide stream can here be split into two substreams as described in DE-A 11 47 214.

The reaction pressure in the process of the invention is from 210 to 250 bar. At lower pressure the space-time yield is insufficient for economic operation, and at higher pressures the technical difficulty of maintaining the pressure rises disproportionately. Preference is given to a pressure of from 215 to 230 bar, and the temperature can be from 50 to 150° C., preferably from 60 to 110° C.

The molar ratios of the starting materials methanol and carbon monoxide can vary within wide limits, for example from 2:1 to 0.5:1, preferably from 1.5:1 to 1:1.

The reaction can occur in reactors such as vertical reaction vessels, but also in tube reactors. Vertical reactors having internal cooling systems or jacket coolers are particularly advantageous. The reaction can be carried out in one reaction vessel, but advantageously in a cascade of reaction vessels in series. This cascade can have a temperature profile with the highest temperature in the first reaction vessel and the lowest temperature in the last vessel.

The conversion in the reaction can be controlled via the residence time of the reactants in the reactor. High final conversions reduce the amounts of starting materials which have to be recirculated to the reaction after the work-up. CO conversions of from 85 to 99% have been found to be useful.

The reaction solution obtained according to the invention can be worked up in a manner known per se. In general, a depressurization and residual gas removal is followed by distillation of the liquid constituents, with the methanol thus obtained being able to be recirculated to the reaction. Methyl formate can be hydrolyzed to formic acid in a known manner.

By means of the process of the invention, a high space-time yield of above 800 g/l. h at a final methyl formate concentration of above 97% by weight (prior to work-up) can be achieved at low catalyst concentrations which significantly reduce the feedstock costs.

The amount of organic salts in the distillation bottoms is considerably lowered and thus allows cheaper disposal.

Furthermore, the use of potassium methoxide as catalyst allows salt-free operation, ie. no salt deposits are formed on heat exchangers, pipes or valves, if the methyl formate content of the reaction solution during the reaction is limited to at most 95% by weight.

In addition, it was unexpectedly found that operation of the process of the invention on an industrial scale leads, owing to the significantly less frequent encrustation of heat exchangers, pipes and valves compared with the prior art, to the down times of the plant necessary for their removal being able to be considerably reduced. This leads in turn to higher availability of the plant and thus to a higher annual capacity.

EXAMPLES

Examples 1 to 6

Four tube reactors connected in series (2 m×45 mm, V=3.15 1) were operated in an upflow mode. Carbon monoxide was metered into the first reactor through a nozzle. The reactors had an internal heat exchanger pipe. The starting compounds could be individually metered into each reactor. The reaction mixture could be taken off after each individual reactor. The catalyst was metered into the reactor 1 (R1) in methanol solution and methanol was fed into R1. The reaction pressure was 220 bar.

The Table below shows the essential reaction data. CO was introduced either into R1 or into both R1 and reactor 2 (R2).

The product was analyzed for methyl formate by gas chromatography and by wet methods. The conversion is based on methanol used. STY is the space-time yield, based on the total volume of all reactors used in the particular case. NaOMe is sodium methoxide, KOMe is potassium methoxide and MeFo is methyl formate. The amount of salt obtained after the distillation was significantly reduced compared with experiments using higher catalyst concentrations.

| Ex. No. | Number of reactors | CO [l/h] R1 | CO [l/h] R2 | MeOH [kg/h] | Catalyst [% by wt.] | | T [°C.] measured in the middle of the reactor R1 | R2 | R3 | MeFo in the output [% by wt.] | Conversion [%] | STY [hg/l · h] |
|---|---|---|---|---|---|---|---|---|---|---|---|---|
| 1 | 4 | 2400 | — | 3.50 | 0.11 | NaOMe | 100 | 90 | 90 | 98.0 | 96.3 | 0.53 |
| 2 | 4 | 3350 | 500 | 4.80 | 0.16 | NaOMe | 100 | 90 | 90 | 97.2 | 94.9 | 0.71 |
| 3 | 3 | 4750 | — | 4.91 | 0.20 | NaOMe | 100 | 85 | 80 | 97.9 | 96.1 | 0.96 |
| 4 | 3 | 3510 | — | 5.27 | 0.13 | NaOMe | 100 | 90 | 85 | 88.2 | 80.0 | 0.86 |
| 5 | 3 | 4750 | — | 5.20 | 0.12 | NaOMe | 100 | 90 | 80 | 75.1 | 61.7 | 0.65 |
| 6 | 2 | 3000 | — | 4.80 | 0.15 | NaOMe | 100 | 90 | — | 80.9 | 69.3 | 0.68 |
| 7 | 2 | 2509 | — | 4.80 | 0.15 | NaOMe | 100 | 96 | — | 74.4 | 60.8 | 0.59 |
| 8 | 2 | 2140 | — | 2.32 | 0.14 | NaOMe | 95 | 80 | — | 96.2 | 93.1 | 0.66 |
| 9 | 2 | 3003 | — | 4.09 | 0.12 | NaOMe | 95 | 80 | — | 84.1 | 73.8 | 0.61 |
| 10 | 3 | 3975 | 655 | 4.89 | 0.20 | KOMe | 100 | 90 | 65 | 98.2 | 96.7 | 0.96 |
| 11 | 2 | 1333 | 947 | 2.42 | 0.17 | KOMe | 95 | 80 | — | 94.6 | 90.3 | 0.67 |
| 12 | 2 | 1380 | 623 | 2.38 | 0.14 | KOMe | 95 | 80 | — | 88.5 | 80.4 | 0.59 |
| 13 | 1 | 2789 | — | 2.89 | 0.19 | KOMe | 80 | — | — | 95.3 | 91.5 | 0.81 |

We claim:

1. A process for the continuous preparation of methyl formate by reaction of carbon monoxide and methanol under elevated pressure and elevated temperature in the presence of an alkali metal methoxide, wherein the reaction is carried out at a pressure of from 210 to 250 bar, and in the presence of from 0.05 to 0.2% by weight of alkali metal methoxide, based on methanol.

2. The process defined in claim 1, which is carried out at a pressure of from 215 to 230 bar.

3. The process defined in claim 1, which is carried out at a temperature of from 50 to 150° C.

4. The process defined in claim 1, wherein the alkali metal methoxide is potassium methoxide.

5. The process defined in claim 2, which is carried out at a temperature of from 50 to 150° C.

6. The process defined in claim 2, wherein the alkali metal methoxide is potassium methoxide.

7. The process defined in claim 3, wherein the alkali metal methoxide is potassium methoxide.

8. The process defined in claim 5, wherein the alkali metal methoxide is potassium methoxide.

* * * * *